US006565533B1

(12) United States Patent
Smith et al.

(10) Patent No.: US 6,565,533 B1
(45) Date of Patent: May 20, 2003

(54) INOCULATION APPARATUS AND METHOD

(75) Inventors: David F. Smith, Santana de Parnaiba (ES); Jackie Green, O'Fallon, MO (US); James Paul Thaxton, Jr., Starkville, MI (US)

(73) Assignee: Novus International, Inc., St. Louis, MO (US)

( * ) Notice: Subject to any disclaimer, the term of this patent is extended or adjusted under 35 U.S.C. 154(b) by 0 days.

(21) Appl. No.: 09/489,546

(22) Filed: Jan. 21, 2000

(51) Int. Cl.[7] .............................................. A61M 37/00

(52) U.S. Cl. ....................................... 604/144; 604/156

(58) Field of Search ................................ 604/506, 131, 604/143, 144, 147, 152, 156

(56) References Cited

U.S. PATENT DOCUMENTS

| | | |
|---|---|---|
| 2,319,938 A | 5/1943 | Markins |
| 2,477,752 A | 8/1949 | Kiss |
| 2,561,027 A | 7/1951 | Liesch |
| 2,757,375 A | 7/1956 | Rieutord et al. |
| 3,021,119 A | 2/1962 | Van Der Burgt |
| 3,159,384 A | 12/1964 | Davis |
| 3,295,524 A | 1/1967 | Parker |
| 3,377,989 A | 4/1968 | Sandhage et al. |
| 3,385,570 A | 5/1968 | Pijls et al. |

(List continued on next page.)

FOREIGN PATENT DOCUMENTS

| | | |
|---|---|---|
| FR | 2 276 839 | 7/1974 |
| GB | 1582511 | 1/1981 |
| GB | 2071501 A | 9/1981 |
| GB | 2126093 A | 3/1984 |
| WO | WO94/01147 A2 | 1/1994 |
| WO | WO01/03605 A1 | 1/2001 |

OTHER PUBLICATIONS

International Search Report in Application No. PCT/US 01/01680 dated Sep. 5, 2001.

*Primary Examiner*—Brian L. Casler
*Assistant Examiner*—Kevin C. Sirmons
(74) *Attorney, Agent, or Firm*—Senniger, Powers, Leavitt & Roedel

(57) ABSTRACT

An inoculation device and method are provided. The device includes a hypodermic syringe with a hollow needle that is positioned to inject a small animal in its abdominal area with an inoculant. A work platform supports the animal during inoculation in a back down, face up orientation. Air flow sensing activation mechanism is positioned adjacent a portion of the animal. When the animal is moved into contact with the activation mechanism, drive connected to the hypodermic syringe moves the needle forward to penetrate the animal after which the inoculant is injected.

21 Claims, 6 Drawing Sheets

U.S. PATENT DOCUMENTS

| | | | | | |
|---|---|---|---|---|---|
| 3,465,717 | A | | 9/1969 | Hein | |
| 3,502,079 | A | | 3/1970 | Simmons et al. | |
| 3,544,074 | A | | 12/1970 | Karpacheva et al. | |
| 3,593,714 | A | | 7/1971 | Lyon | |
| 3,594,285 | A | | 7/1971 | Noren | |
| 3,635,446 | A | | 1/1972 | Kurosawa | |
| 3,641,998 | A | | 2/1972 | Lyon et al. | |
| 3,727,614 | A | | 4/1973 | Kniazuk | |
| 3,774,578 | A | | 11/1973 | Randolph et al. | |
| 3,964,481 | A | | 6/1976 | Gourlandt et al. | |
| 4,007,739 | A | | 2/1977 | Bron et al. | |
| 4,040,388 | A | | 8/1977 | Miller | |
| 4,108,176 | A | | 8/1978 | Walden | |
| 4,114,619 | A | | 9/1978 | Wagner | |
| 4,177,810 | A | | 12/1979 | Gourlandt | |
| 4,276,879 | A | | 7/1981 | Yiournas | |
| 4,316,672 | A | | 2/1982 | Kerscher | |
| 4,469,047 | A | | 9/1984 | Miller | |
| 4,515,590 | A | * | 5/1985 | Daniel | 604/144 |
| 4,533,255 | A | | 8/1985 | Gronholz | |
| 4,593,646 | A | | 6/1986 | Miller et al. | |
| 4,664,526 | A | | 5/1987 | Scheffler et al. | |
| 4,681,063 | A | | 7/1987 | Hebrank | |
| 4,681,565 | A | | 7/1987 | Gourlandt | |
| 4,732,487 | A | | 3/1988 | Pollard | |
| 4,758,227 | A | | 7/1988 | Lancaster et al. | |
| 4,848,917 | A | | 7/1989 | Benin et al. | |
| 4,863,443 | A | | 9/1989 | Hornung | 604/289 |
| 4,903,635 | A | | 2/1990 | Hebrank | |
| 4,928,628 | A | | 5/1990 | Gassman et al. | |
| 4,928,629 | A | | 5/1990 | Trampel | |
| 4,967,939 | A | | 11/1990 | Taylor | |
| 4,990,135 | A | | 2/1991 | Truesdale, Jr. | |
| 4,993,597 | A | | 2/1991 | Evers, et al. | |
| 5,045,074 | A | | 9/1991 | Satterfield et al. | |
| 5,056,464 | A | | 10/1991 | Lewis | |
| 5,136,979 | A | | 8/1992 | Paul et al. | |
| 5,158,038 | A | | 10/1992 | Sheeks et al. | |
| 5,176,101 | A | | 1/1993 | Paul et al. | |
| 5,199,952 | A | | 4/1993 | Marshall et al. | |
| 5,240,323 | A | | 8/1993 | Haber et al. | |
| 5,242,388 | A | | 9/1993 | Marshall, Sr. | |
| 5,311,841 | A | | 5/1994 | Thaxton | 604/51 |
| 5,312,353 | A | * | 5/1994 | Boggess et al. | 604/144 |
| 5,339,766 | A | | 8/1994 | Phelps et al. | |
| 5,380,087 | A | | 1/1995 | Haber et al. | |
| 5,395,593 | A | | 3/1995 | Martin | |
| 5,427,791 | A | | 6/1995 | Ahmad et al. | |
| 5,438,954 | A | | 8/1995 | Phelps et al. | |
| 5,468,227 | A | | 11/1995 | Haskell | |
| 5,549,574 | A | | 8/1996 | Townsend | |
| 5,637,094 | A | | 6/1997 | Stewart, Jr. et al. | |

* cited by examiner

INOCULATION APPARATUS AND METHOD

BACKGROUND OF THE INVENTION

The invention relates to an apparatus for inoculating small animals, e.g., fowl or poultry such as chickens, turkeys, guineas, geese, ducks, pheasants, quails, etc. when they are young.

Domestically raised poultry are subject to various diseases and infections after hatching. For the effective raising of such poultry, they need to be inoculated to reduce loss of poultry and to insure efficient growth. When a disease or infection starts in a flock, it can quickly spread to the remainder of the birds causing catastrophic loss, sometimes of the entire flock. Oftentimes the profit margin on poultry is low, so even the loss of a few birds or their failure to grow efficiently, can have a substantial adverse effect on overall profits. There is thus a need for an apparatus to quickly and efficiently inoculate a large number of birds with a high level of confidence that all or substantially all of the birds have been effectively inoculated. For example, it is desired to effectively inoculate at least 99% of chicks born into a flock.

Devices for inoculating poultry by automatic injection of inoculants through a hypodermic needle and syringe are well known in the art. Such a device and corresponding method are disclosed in U.S. Pat. No. 5,311,841, (incorporated herein by reference). The disclosed method provides a major advance in the effective inoculation of poultry when they are in the chick stage. The inoculation, according to the disclosed method, is done when the chicks are young and still have their yolk sacs. The yolk sac is relatively small on the major surface and thin and the needle needs to be accurately directed and positioned to insure the tip of the needle is located in the sac when the inoculants are injected. In order to handle the large number of birds encountered at a typical large poultry farm, the device needs to be quick and efficient to use. However, the bird needs to be properly positioned relative to the injection needle and relative to the ground and held in that position for proper inoculation. Also, the inoculation device needs to include a positive trigger mechanism to automatically activate the syringe and needle.

Because many birds will be processed in succession, there is a need to sanitize the needle without stopping inoculation to effect sanitizing. It is preferred that the needle be continuously sanitized with minimal clean up and waste of disinfectant. Sanitization is known, see for example, U.S. Pat. No. 4,515,590 wherein a sprayer is used to sanitize the needle. This system however requires cleanup of the spray from inside the housing and is sprayed at intervals. Also, the exterior surface of the needle is not wiped during such spray cleaning.

The working environment in poultry farms is oftentimes wet. This presents concerns for worker safety particularly when using power operated devices since many are powered at least in part by electricity. It would be desirable to eliminate the risk of electrical shock to workers by providing an inoculator that can be operated without the use of electricity and still provide the ability to have an effective automatic operation control system.

Various types of medicaments are used for inoculation. Some medicaments are mixed together so that only one injection is required to complete the inoculation. However, it has been found that the medicaments can physically separate whereby the inoculant is not uniform throughout the container. The inoculant needs to be agitated or otherwise mixed, preferably continuously, to insure uniformity and thereby effectiveness of the inoculation. Thus, there is a need for an inoculating device that insures uniformity of inoculant when injected. Further, the agitation is desirably achieved without the use of electricity at the inoculator.

Many devices are available for such inoculations but have one or more of the above described drawbacks. Thus, there is a need for an apparatus and method for improved inoculations.

SUMMARY OF THE INVENTION

Among the several objects and features of the present invention may be noted the provision of an inoculation apparatus that improves upon the currently available devices; the provision of an inoculation apparatus that is easy and efficient to use; the provision of an inoculation apparatus that reduces the need for stopping inoculation to sanitize the needle and that provides an improved sanitizer that can clean the needle between each injection; the provision of an inoculation apparatus that is effective and efficient in inoculating large numbers of birds in a short period of time; the provision of an inoculation apparatus that provides improved positioning of the bird relative to the needle and horizontal (the ground) for inoculation; the provision of an inoculation apparatus which reliably triggers movement of the hypodermic needle to the extended or inoculating position; the provision of an inoculation apparatus that eliminates the risk of electrical shock while providing an automatic operation control system; and the provision of a method of inoculation that stabilizes and enhances the inoculation target area of the bird.

One aspect of the present invention includes the provision of an apparatus for inoculating small animals. The apparatus includes a housing and a movable hypodermic syringe mounted in the housing. A hollow needle is mounted on the syringe. A retention device is mounted on the housing and is adapted for positioning an animal to be injected relative to the hollow needle. Drive means is mounted in the housing and is connected to the hypodermic syringe and operable to selectively move the needle between an extended position and a retracted position. A conduit for flow of fluid has an opening for flow of fluid therethrough is provided. The opening is positioned relative to the needle so that an object in the drive path of the needle may partially block the opening to restrict flow of fluid through the opening A pressure sensor is operably connected to the conduit and the drive means and is operable to detect pressure change in the conduit caused by the partial blockage of the opening to activate the drive means whereby the drive means moves the needle to the extended position in response to the change in pressure.

A further aspect of the present invention includes an apparatus for injecting small animals having an abdominal area with a fluid. The apparatus includes a housing with a hypodermic syringe movably mounted therein. A hollow needle is mounted on the syringe. A cradle is mounted on the housing and is adapted for positioning an animal to be injected in a face up position relative to the hollow needle so that an abdominal area of the animal is exposed for penetration by the hollow needle. Drive means is mounted in the housing, is connected to the syringe and is operable to selectively move the needle between an extended position and a retracted position. A guide is mounted on the housing and has an elongate bore adapted to receive the hollow needle therein for movement between the extended and retracted positions of the hollow needle.

Another aspect of the present invention involves the provision of a method of injecting an animal having a back and an abdomen with a fluid. An animal is positioned adjacent to a hollow needle whereby a portion of the abdomen is positioned for penetration by the hollow needle. The hollow needle has a longitudinal axis and is movable between an extended position and a retracted position in a plane that is generally parallel to the longitudinal axis of the needle and the plane of movement of the needle is generally parallel to the back of the animal. The needle is moved to its extended position and penetrates the abdomen portion. The animal is injected with a fluid and the needle is moved to its retracted position.

A still further aspect of the present invention involves the provision of an apparatus for injecting small animals with a fluid. The apparatus includes a housing with a hypodermic syringe movably mounted therein. A hollow needle is mounted on the syringe. A retention device is mounted on the housing and is adapted for positioning an animal to be injected relative to the hollow needle. The retention device includes a cradle extending from the housing and opening generally upwardly, the cradle has a portion defining an opening adjacent the housing for receiving a posterior portion of the animal to facilitate positioning the animal relative to the needle. Drive means is mounted in the housing and connected to the syringe and is operable to selectively move the needle between an extended position and a retracted position.

The present invention involves an apparatus that includes a housing having an end wall. A hypodermic syringe is movably mounted in the housing and a hollow needle is mounted on the syringe and movable therewith, the needle being movable in a first plane through an opening in the end wall. Drive means is operably connected to the syringe to selectively effect movement of the needle between an extended position and a retracted position in the first plane. A retention platform is mounted on the end wall and projects outwardly from the end wall and has an upwardly opening elongate trough with a longitudinal axis. The trough has an animal support surface spaced from the needle opening. The plane of movement of the needle is at an angle relative to the longitudinal axis of the trough in the range of about −5° through about +5°. The support surface and needle are positioned such that an animal to be inoculated can be positioned face up on the support surface and relative to the needle whereby the needle in its extended position can penetrate an abdominal area of the animal.

The present invention also involves an apparatus that includes a housing with a hypodermic syringe movably mounted therein. A hollow needle is mounted on the syringe. A work platform is mounted on the housing and is adapted for positioning an animal to be injected relative to the hollow needle. Drive means is mounted in the housing and is connected to the hypodermic syringe and is operable to selectively move the needle between an extended position and a retracted position. A guide tube is mounted on the housing adjacent the needle and is adapted for the needle to move through between the extended and retracted positions of the needle. A porous member is mounted in the guide tube and surrounds a portion of the needle when the needle is in its extended position. A source of sterilizing fluid is provided. A conduit is in flow communication with the porous member and the source of sterilizing fluid and is adapted to provide a sterilizing fluid from the source of sterilizing fluid to the porous member for application to the needle.

The present invention also involves the provision of an apparatus for injecting small animals with a fluid. The apparatus includes a housing with a hypodermic syringe movably mounted therein. A hollow needle is mounted on the syringe. A work platform is mounted on the housing and is adapted for positioning an animal to be injected relative to the hollow needle. First drive means is mounted in the housing and is connected to the hypodermic syringe and operable to selectively move the needle between an extended position and a retracted position. A support is mounted on the housing and a container of inoculant is retained in the support. Agitator means is carried by the housing and is operably associated with the support for periodically inducing vibration in the support and the support is operable to move the container by moving the support to agitate the inoculant.

Other objects and features will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
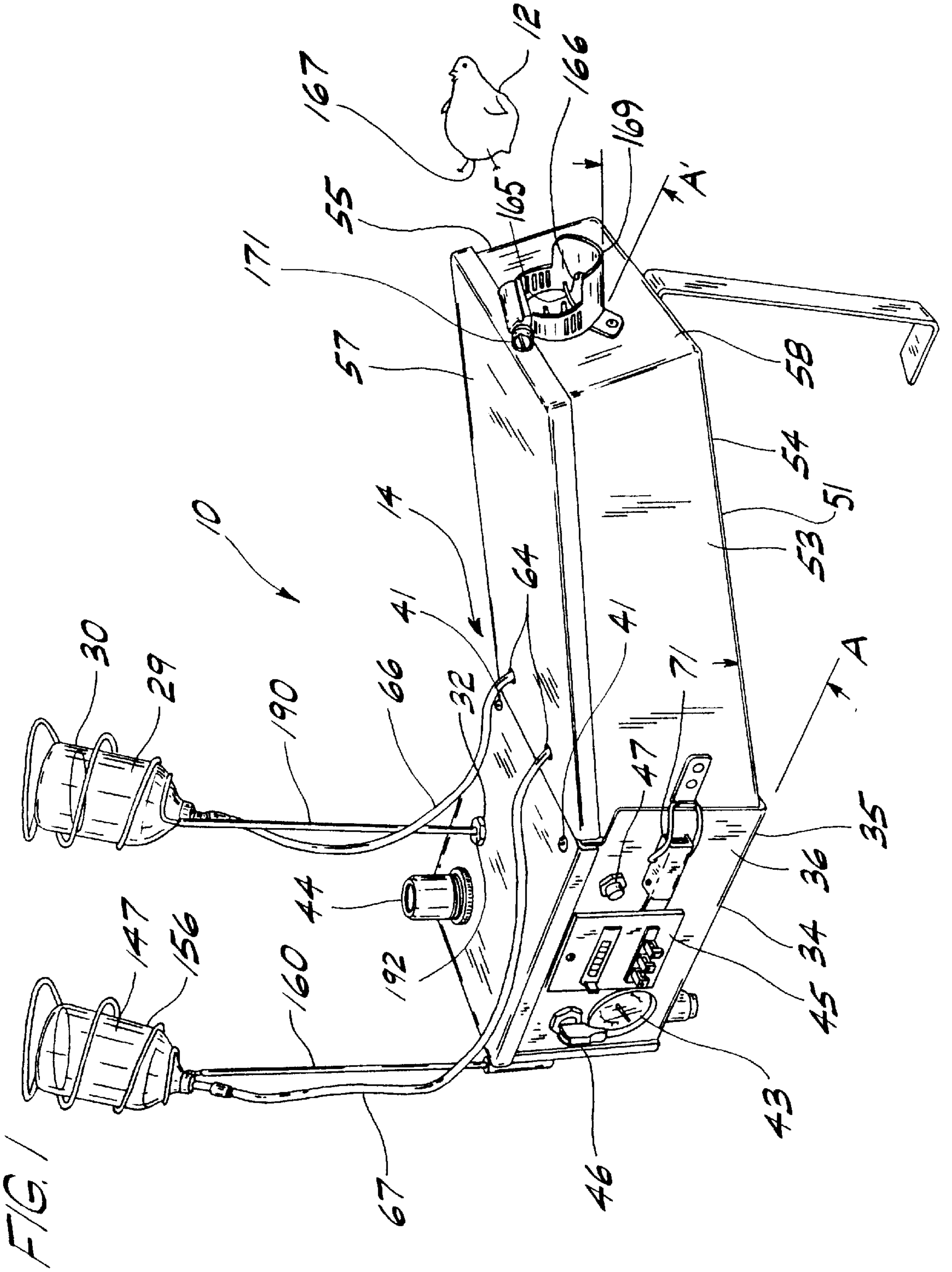
FIG. 1 is a perspective view of an apparatus for inoculating small animals.
Figure 2:
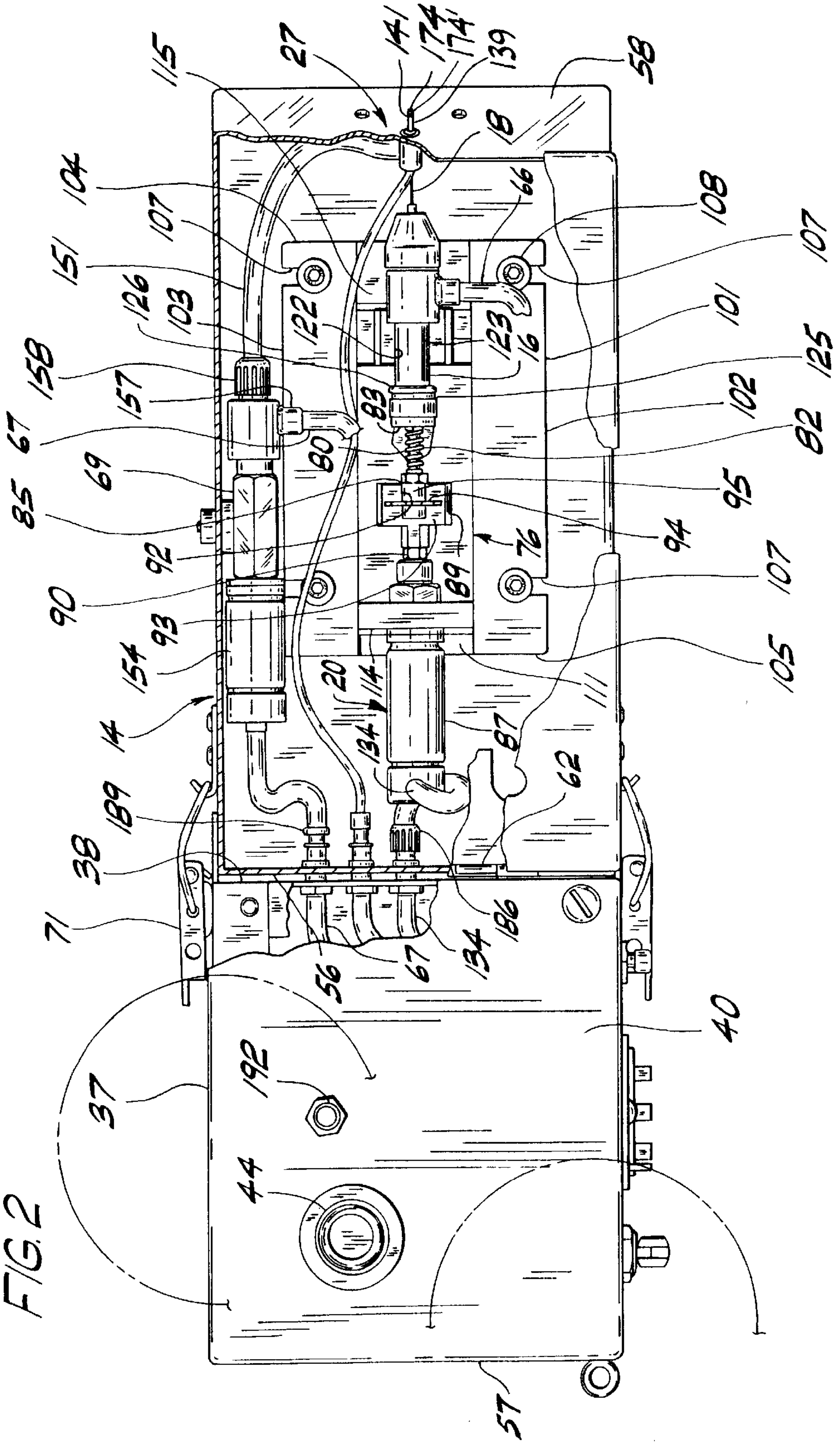
FIG. 2 is a fragmentary plan view of the inoculating apparatus with portions broken away to illustrate components mounted inside the apparatus.
Figure 3:
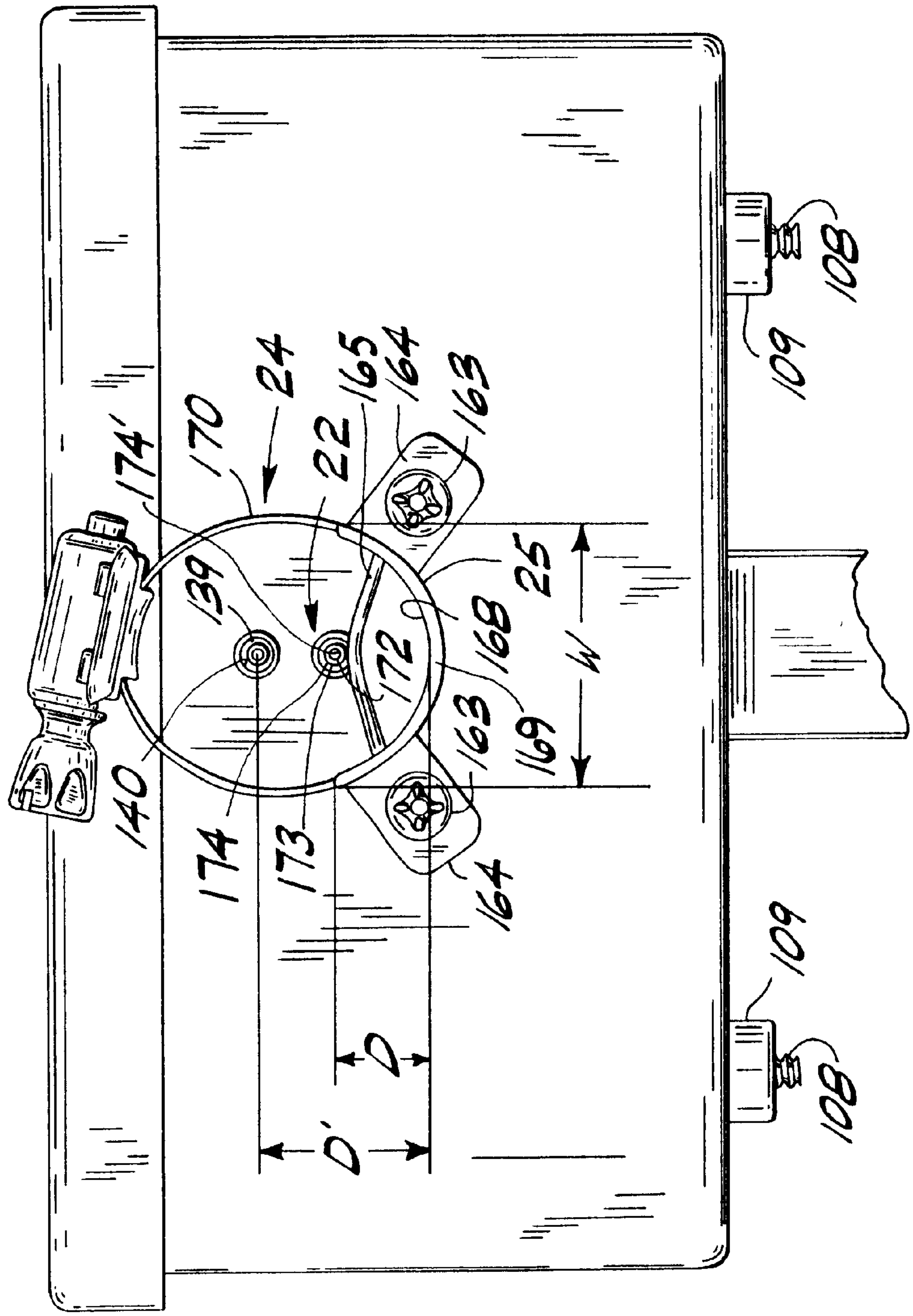
FIG. 3 is a front end view of the apparatus showing a cradle on one end of the apparatus.
Figure 5:
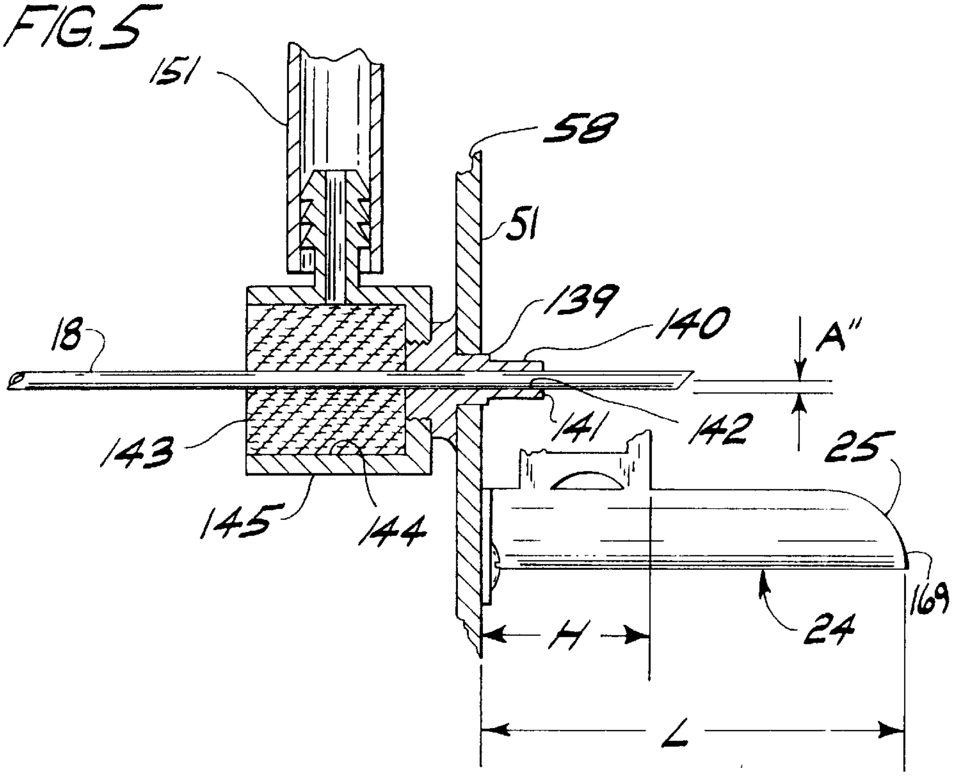
FIG. 5 is an enlarged fragmentary view of the hypodermic needle sanitizing device shown in side elevation.
Figure 7:
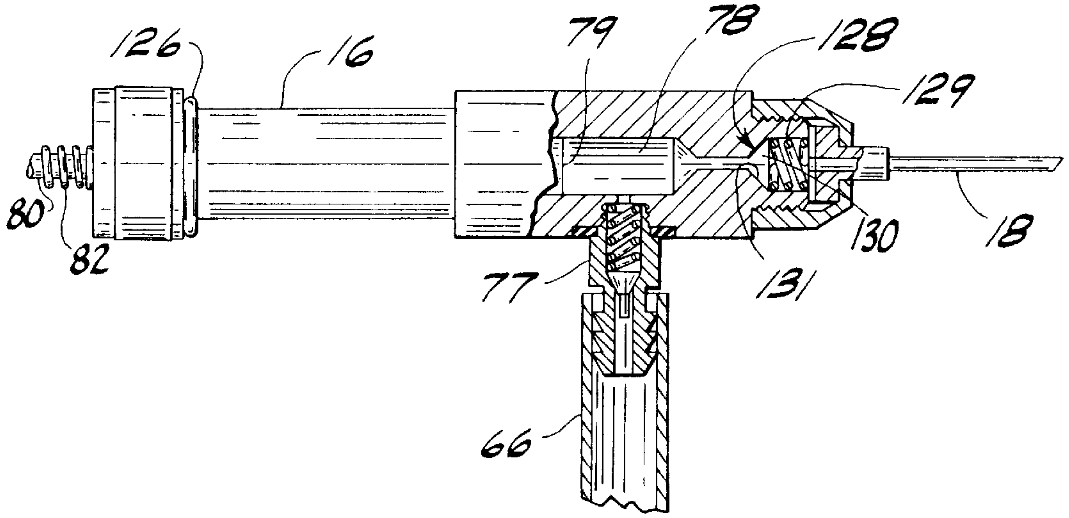
FIG. 7 is an enlarged view of the; syringe with portions broken away to show internal detail of the syringe.

The reference numeral 10 (FIG. 1) designates generally apparatus for inoculating small animals 12 such as poultry, including, chickens, turkeys, ducks, geese, guineas, pheasants, quails, etc. Preferably, poultry is inoculated when it is young and still has a yolk sac that is positioned in the abdomen of the bird. The apparatus 10 generally includes a housing or frame 14, a syringe 16, a hollow needle 18, a drive 20 operable to move the needle 18 along a drive path between an extended position and a retracted position (FIGS. 1, 2 and 7). The apparatus 10 also includes a trigger mechanism, designated generally as 22, that actuates movement of the needle 18 (FIG. 3). A retention or work platform 24 which includes a cradle 25 is provided in which the animal 12 is placed for locating it in the drive path relative to the needle 18 for inoculation when the needle moves to its extended position along the drive path (FIGS. 3 and 5). To maintain the needle 18 sanitized, a needle sanitizer, designated generally as 27, is provided. Inoculant 29 is contained in a container 30 and is fed to the needle 18 through the syringe 16 as is known in the art. The inoculant 29 in the container 30 is maintained mixed by an agitation device, designated generally as 32, carried by the housing 14.

The housing 14 includes a first case 34 for containing the operation control system (hereinafter described). The case 34 includes six walls (designated respectively by the reference numerals 35–40) and is a generally rectangular solid in shape. One or more walls can be removable to provide access to the interior of the case 34. As shown, the top wall 40 and one end wall 39 are connected together forming a lid that can be separated from the remainder of the case walls by removal of the screws 41. A pressure gauge 43 is mounted in a side wall 36 so it can be viewed by an operator. Also, adjustable controls, including the pressure regulator knob 44, the counter 45, the master control switch 46 and a reset operator 47 are mounted on the case 34 and as shown, the knob 44 is mounted above the wall 40 and the counter, control switch and reset operator are mounted on the wall 36 for manipulation by the operator of the apparatus.

The housing 14 also includes a second case 51. Preferably, the second case 51 houses various moving parts and operation control devices (hereinafter described) of the apparatus 10 and like the case 34, has six walls (designated respectively by the reference numerals 53–58). Preferably, the top wall 57 is movable or removable to provide access to the interior 60 of the second case 51 and the parts mounted therein. As shown, the top wall 51 is a lid hingedly mounted on the end wall 56 with a hinge 62 for pivoting movement between open and closed positions. Two ports 64 are provided through the top wall 57 for conduits 66, 67 to extend through to be connected to the syringe 16 and a disinfectant pump (hereinafter described). Preferably, the housing 14 is made of metal such as stainless steel which is easy to clean and is corrosion resistant. The cases 34, 51 are joined together at a joint by suitable fasteners, such as toggle clamps 71. The first and second cases 34, 51 can thus be separated for maintenance, cleaning, etc. The second case 51 preferably contains no control circuit devices that can be damaged by cleaning and is separated from the first case 34 for cleaning, e.g., by immersion in a cleaning liquid. The case 51 has a bottom wall 54 that is angled from horizontal (the ground) at an angle A in the range of about 20° through about 60° and preferably in the range of about 30° through about 45°.

As seen in FIG. 2 the apparatus 10 includes the hypodermic syringe 16, such as a model 516000 syringe made by Wings. The syringe 16 is mounted in a guide support 76 for linear movement between an extended position and a retracted position. The syringe 16 has the hollow hypodermic needle 18 mounted on the forward end (FIG. 7). The needle 18 is connected in fluid flow communication with a metering chamber 78 in the syringe 16. The metering chamber 78 is in turn connected in fluid flow communication to the source of inoculant 29 or vaccine, which is shown as the container 30, via the conduit 66. The inoculant 29 flows by the influence of gravity from the container 30 to the syringe 16 metering chamber 78 or could be pumped if desired. Pumping can be done at least in part by negative pressure created in metering chamber 78 when a piston 79 moves from its extended position to its retracted position. A check valve 77 is provided between the conduit 66 and metering chamber 78 to prevent flow of inoculant from the chamber back into the conduit during inoculation.

The syringe 16 includes the piston 79 with a plunger 80 extending out of the rearward end of the syringe. The piston 79 is spring loaded to return the piston to a rearward or retracted position. A spring 82 is positioned between a syringe housing 83 and a shoulder formed by a connector 85 and is normally compressed providing force to help return the piston 79 to the retracted position. Drive 20 is provided and is operably connected to the syringe 16 to effect linear movement of the syringe 16 and needle 18 between their retracted positions (shown in FIG. 2) and extended positions. A preferred drive 20 includes a pneumatic cylinder 87 that is connected to the syringe 16 by the connector 85. Preferably the connection provides for easy connection and disconnection of the syringe 16 from the cylinder 87. As shown, the cylinder 87 has a coupling 89 connected to its piston rod 90. The coupling 89 is preferably made of a plastic such as nylon. The coupling 89 includes an open channel 92 which receives the syringe connector 85. The connector 85 and coupling 89 are retained against relative longitudinal movement by an E-ring 93 mounted on the plunger 80 and received in a groove 94 in the coupling 89. This arrangement permits easy disconnection by moving the connector 85 and E-ring 93 out through the opening 95 of the channel 92. The width of the opening 95 is smaller than the diameter of the connector 85 whereby the connector 85 is releasably retained in the coupling 89.

A base plate 101 is mounted in the case 51 in a manner that will permit its selective movement. The base plate 101 is mounted so it can be moved transversely of the case 51. As seen in FIG. 2, the base plate 101 is generally rectangular having opposing longitudinal side edges 102, 103 and opposing end edges 104, 105. The side edges 102, 103 each have a plurality of spaced slots 107 extending transversely into the base plate 101 from a respective side edge 102, 103. A fastener 108, such as a screw, extends through each slot 107 and is received through a respective aperture in the bottom wall 54 and is secured in place, as with nuts 109, thereby securing the base plate 101 in place inside the case 51. The slots 107 allow the base plate 101 to be positioned in a desired transverse position. The base plate 101 also has an elongate groove 111 extending longitudinally of the base plate 101 between the end edges 104, 105.

The guide support 76 is secured inside the case 51 in any suitable manner for selective longitudinal movement in the case. The guide support 76 includes a generally U-shaped frame comprising a pair of upright legs 114, 115 and a base 116. As shown, the base 116 is received in the groove 111 for linear movement therein. The base 116 has an elongate slot 118 therethrough. A mechanical fastener such as a stud 119 secured in the base plate 101 extends through the slot 118. A threaded fastener such as a wing nut 120 is threaded onto the stud 119 and when tightened, fixes the longitudinal position of the guide support 76 on the base plate 101 in the case 51. The edges of the groove 111 prevent rotational movement of the guide support 76 about the stud 119 on the base plate 101. The transverse movement of the base plate 101 and the longitudinal movement of the guide support 76 on the base plate 101 permit the transverse and longitudinal adjustment of the position of the guide support 76 and components mounted thereon including the needle 18. Also, the base plate 101, guide support 76 and components are removable from the housing 51 facilitating repair, maintenance and cleaning.

The cylinder 87 is mounted on the leg 114. The syringe 16 is movably mounted on the leg 115 in a race 122 for linear movement therein. The race 122 has an open top 123 and has a round through bore with a diameter slightly larger than the diameter of the syringe 16 therein for a slip fit. The open top 123 is smaller transversely than the syringe 16 diameter so that the syringe is releasably retained in the race 122. Preferably the race 122 is made from a low friction material such as Delrin, a self lubricating plastic. The cylinder 87, piston and piston rod 90 are coaxial with the syringe 16, piston 79 and needle 18. Movement of the cylinder piston forward first moves the syringe 16 forward in the race 122 until a flange 125 on the syringe 16 engages the guide support 76. A resilient cushion 126 such as an O-ring can be positioned on the syringe 16 between the flange 125 and the guide support 76 to cushion the impact therebetween. The forward motion of the syringe 16 and needle 18 stop when the flange 16 (or O-ring 126) engages the guide support 76.

After forward movement of the syringe 16 and needle 18 stop, the forward motion of the cylinder piston rod 90 continues. With the forward motion of the syringe 16 stopped, the syringe piston 79 then begins to move forward within the syringe 16 in the chamber 78 compressing the spring 82. Inoculant 29 contained in the syringe chamber 78 is pressurized and ejected through the needle 18 and into the animal to be inoculated. As seen in FIG. 7, the syringe 16 includes a valve 128. The valve 128 is preloaded with the bias of a spring 129 to hold the valve element 130 in engagement with the valve seat 131. When a predetermined pressure is reached in the syringe chamber 78, the bias is overcome and the inoculant in the chamber 78 flows through the needle 18. The use of such a pressure release valve 128 prevents the inoculant 29 from flowing through the needle 18 until the predetermined pressure is attained thereby preventing leaking. A pre-measured dose of inoculant 29 is delivered because the syringe 16 is a positive displacement pump. The retraction of the needle 18 from its forward most position is fast enough to prevent drawing liquid contents of the animal back into the needle. The syringe 16 can have the volume of the inoculant chamber changed, as is known in the art, for example by providing a syringe piston 79 of a different length changing the volume of the syringe chamber 78. A typical inoculation dosage for a chick is in the range of about 0.1 ml through about 0.5 ml and preferably about 0.2 ml.

Figure 4:
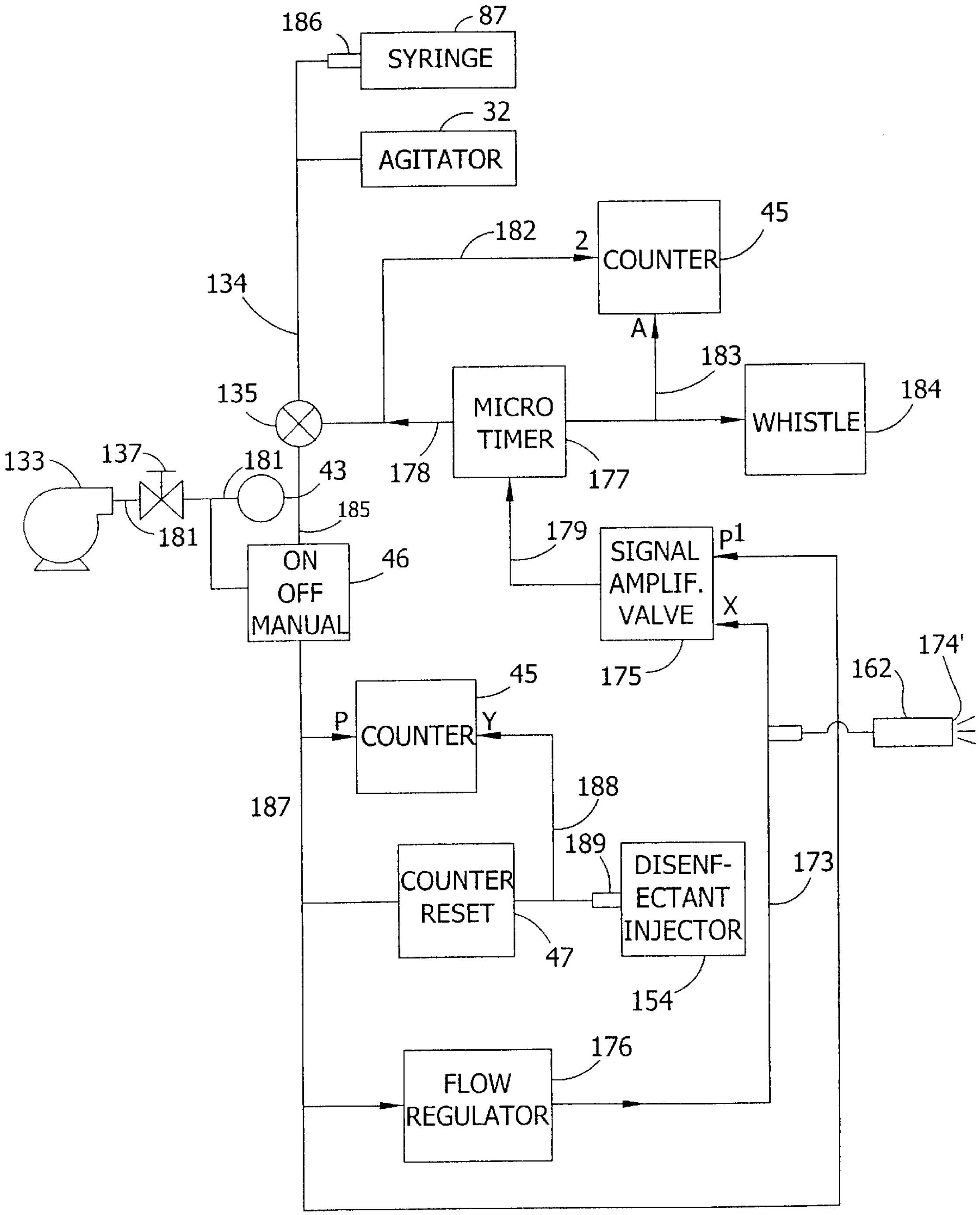
FIG. 4 is a schematic diagram of the control circuit and cylinders used to operate the apparatus.

Preferably the cylinder 87 is a single acting cylinder with spring return. Pressurized air from an air source 133 is supplied from the source through a pressure regulator 137, a conduit 134 and a control valve 135 to selectively move piston rod 90 of the cylinder 87 to its extended position (FIGS. 2 and 4). The spring in the cylinder 87 will return the piston 79, needle 18 and syringe 16 to their retracted positions when the pressurized air in the cylinder is released through an exhaust port in the on-off switch 46. Also, the cylinder 87 could be a double acting cylinder, if desired, using pressurized air for extension and retraction.

A needle guide tube 139 is secured to the case 51 and is positioned to permit the needle 18 to move therethrough between the extended and retracted positions of the needle (FIGS. 2, 3 and 5). The guide tube 139 has a nipple 140 that projects outwardly from the end wall 58 a distance in the range of between about 0.5 through about 0.75 cm. The guide tube 139 is suitably secured to the wall 58 such as by welding. The elongate bore 142 through the guide tube 139 is coaxial with the needle 18 and the needle is preferably positioned in the approximate center of the bore 142. The retracted position of the needle 18 preferably leaves the needle point inside the guide tube 139. For chicks, the needle 18, in its extended position, extends from the distal end 141 of the guide tube 139 a distance in the range of about 2 mm through about 3 mm as measured from the rearward end of the bevel on the needle end to the distal end 141 of the guide tube 139.

The nipple 140 is positioned above the upwardly facing support surface 168 of the cradle 25 a distance D' in the range of about 1.5 cm and about 2.0 cm as measured from the lower most disposed portion of the surface 168. The nipple 140 is preferably generally round in transverse cross section and has a diameter in the range of about 0.25 cm through about 0.4 cm at least at the distal end 141.

The apparatus 14 is provided with means 27 for sanitizing the needle 18. As shown in FIG. 5, a porous member 143 is installed or mounted in an enlarged bore 144 in a tubular housing 145. The bores 142, 144 are preferably generally coaxial. The housing 145 is secured to the nipple 140. The porous member 143 is preferably soft for penetration by the needle and can be made of, e.g., polyester felt. Also, it is preferred that the porous member 143 be in contact with the needle 18 to apply disinfectant 147 directly to the needle and wipe the needle of debris. The bore 144 of the housing 145 and hence the porous member 143 are connected in flow communication with a source 148 of disinfectant 147 such as alcohol. The porous member 143 absorbs disinfectant 147 and holds disinfectant metered to it for subsequent application to the needle 18. It is preferred that the disinfectant 147 be fed to the porous member 143 in a positive and metered fashion to insure adequate application but not over application of the disinfectant to the needle 18. A preferred metering system includes a pneumatic positive displacement pump 69 such as piston pump. A suitable pump 69 is a model N700500 made by Wings. The pump 69, when activated, will deliver a predetermined amount of disinfectant 147 to the porous member 143 via a conduit 151 connecting the pump in flow communication with the porous member. It is preferred that the pump 69 be activated by the cycle counter 45, such as a Wings model 501000, to operate the pump sequentially. The counter 45 is operable to count the number of needle movements and hence inoculations. The preferred counter 45 is a count down counter. When a preset number of cycles has been achieved, e.g. 100, the counter 45 activates a valve 153. The valve 153 is shown as part of the counter reset 47. The valve 153 allows air to flow to a pneumatic cylinder 154 connected to the pump 69 to effect a pump stroke and delivery of a predetermined amount of disinfectant to the porous member 143. The pump 69 is in flow communication between the source 156 of disinfectant and the porous member 143 via conduits 151, 67. Preferably, the pump 69 has built in valving to prevent flow of disinfectant 147 to the porous member 143 without pump activation and prevent flow back to the source of disinfectant during pumping. A check valve 157 prevents back flow to the source 156, such as a container, and a pressure release valve 158 is in the outlet of the pump 69. The pressure release valve 158 prevents flow until a predetermined pressure is reached in the pump 69. This prevents flow of disinfectant 147 to the porous member 143 until the pump 69 is activated to pressurize the disinfectant 147 in the pump. The porous member 143 will apply the disinfectant 147 to the needle 18 on every movement of the needle even though the disinfectant is supplied to the porous member incrementally or sequentially. By controlling the feed of disinfectant 147 and applying the disinfectant directly to the exterior of the needle 18, little if any waste of disinfectant occurs and there is little if any disinfectant to clean up.

As shown, the container 156 is mounted in a stand 160 that is suitably mounted on the case 34. The container 156 is positioned at an elevated position relative to the pump 69 and the porous member 143 to allow gravity to induce flow of the disinfectant 147 to the pump 69 and hence the porous member 143. The use of the pump 69 insures positive delivery of disinfectant 147 and also permits intermittent delivery in a controlled manner. As shown, the pump 69 is mounted in the case 51 by suitable securement to the side wall 55.

To insure effectiveness of the inoculation, particularly when injecting into the yolk sac, the bird being inoculated needs to be positively and properly positioned relative to the needle 18. The work platform 24, as best seen in FIGS. 1 and 3 is provided to position the chick 12 relative to the needle 18 for inoculation. The work platform 24 includes the cradle 25 secured to the wall 58 adjacent the guide tube 139, nipple 140 and the trigger mechanism 22, for example with mechanical fasteners 163 through laterally extending ears 164.

The cradle 25 projects outwardly from the wall 58 and is upwardly opening for ease of bird positioning. The cradle 25 is in the shape of a trough that is arcuate in transverse cross section. The cradle 25 is preferably sized and shaped such that when a chick is placed therein, the yolk sac will maintain its shape and position to help insure proper inoculation when the abdomen is placed against the distal end 141 of the nipple 140. For use with chicken chicks, the cradle 25 has a length L of about 3 cm, a width W at the open top of about 3 cm and a depth D of about 1 cm. The cradle 25 is preferably made of metal such as stainless steel to facilitate cleaning.

A hatch or opening 166 is provided at the juncture between the cradle 25 and the end wall 58 and extends longitudinally into the cradle 25 toward a free (e.g., outer or distal) end 169 of the cradle. The opening 166 is positioned in the lower most portion of the cradle 25 and under the nipple 140. The opening 166 facilitates positioning of the bird 12 relative to the needle 18 and the nipple 140 and allows for a more sanitary structure during operation to prevent the collection or build up of vented waste. The opening 166 is shown as an elongate slot and is sized to receive the tail portion or posterior 167 of a chick 12. The opening 166 has a width in the range of between about 0.8 cm through about 1 cm and a length, as measured from the end wall 58, in the range of between about 0.9 cm through about 1.1 cm. A crossbar 165 is secured to the cradle 25 adjacent the end wall 58 and the opening 166 and is preferably arcuate and spaced from the support surface 168 of the cradle. The maximum spacing between the crossbar 165 and the support surface 168 is located above the opening 166 and is in the range of about 0.7 cm through about 0.9 cm. The crossbar 165, support surface 168 and the edges of the opening 166 form a yoke for receiving and restraining the rearward or posterior end 167 of a chick 12 against movement while forcing the chick's tail portion downward and abdomen up to help position the yolk sac.

The cradle support surface 168 is preferably inclined upwardly relative to horizontal. It has been found that having a chick 12 inclined with the head of the chick 12 at the high end as opposed to horizontal reduces struggle by the chick during inoculation. This inclined position is also more ergonomic for the operator. The angle of incline A' is that angle between the longitudinal axis of the cradle 25, which is generally parallel to the lowermost disposed portion or nadir of the support surface 168 extending between the opposite end of the cradle, and horizontal and is in the range of about 20° through about 60° and preferably in the range of about 30° through about 45°. The needle 18 moves in a path generally parallel to or in a plane that extends generally vertically through the longitudinal axis of the cradle 25. It also moves at an angle A" relative to the longitudinal axis of the cradle 25 in the range of about −5° (downwardly and away from the longitudinal axis) through about 5° (upwardly and away from the longitudinal axis) as seen in FIG. 5. The preferred angle A" is in the range of about +1° through about +3°. The chick 12 has a coronal plane that is generally parallel to it backbone. Thus, the coronal plane of the chick 12, when in the cradle 25, is positioned at an angle relative to horizontal in the range of about 20° through about 60° and preferably in the range of about 30° through about 45°.

The work platform 24 includes an arcuate fence 170 secured to and extending between opposite sides of the cradle 25 at the wall end of the cradle. The projection height H (in the longitudinal direction of the cradle 25 as seen if FIG. 5) of the fence is in the range of about 1.5 cm through about 2.0 cm. The fence 170 and the cradle 25 cooperate to form a generally circular ring adjacent to the end wall 58. The diameter of the ring is in the range of between about 3.0 cm through about 4.0 cm and can be adjusted via the screw 171. The fence 170 helps position the bird by surrounding the abdomen area so the abdomen is aligned and constrained for penetration by the needle 18. The needle 18, nipple 140, and the trigger mechanism 22 are positioned inside the ring formed by the fence 170 and cradle 25.

The trigger mechanism 22 is operably connected to a control circuit operable to activate or otherwise trigger movement of the needle 18 between its extended and retracted positions. As seen in FIGS. 3 and 4, the trigger mechanism 22 comprises a conduit 173 in flow communication at one end with the source 133 of pressurized air and extending out through the end wall 58 below the guide tube 139 to a distal end 174 of the conduit. Air flows continuously from the source 133 of pressurized air through a flow passage 172 of the conduit 173 and out through an opening 174' in the distal end of the conduit to help keep the flow passage free of debris. However, it is understood that pressurized air could flow from the environment in through the opening 174' and through the flow passage 172. The distal end 174 of the conduit 173 forms a valve seat at the opening 174' and selectively cooperates with a portion of the animal 12 to form a valve that can at least partially block the flow of air through the flow passage 172. A pressure sensitive valve 175, such as a signal amplifier valve model VL34H20 from Festo, is connected to the conduit 173 and is operable to sense the air pressure therein. When the flow passage 172 is at least partially blocked or obstructed, the air pressure in the conduit 173 will increase. When a predetermined pressure is achieved in the conduit 173, a controller 177, such as a micro timer from Wings, model 552000, will be activated. The controller 177 can include an air flow rate regulator which is adjustable to control the operating speeds of the various cylinders. The sensitivity of activation of the pressure sensitive valve 175 is adjustable by adjusting the air flow through the flow passage 172 with the flow regulator 176, such as a Festo model GR 1/8 that is connected in the conduit 173. Activation of the pressure sensitive valve 175 allows full pressure air to flow through the conduit 187 through the valve 175 to the controller 177. The controller 177 is operably connected to the valve 135 via a conduit 178. When the controller 177 is activated, it in turn activates the valve 135 allowing pressurized air to flow through the conduits 134, 181, 184 from the source 133 to the cylinder 87 urging the cylinder to move the syringe 16 and needle 18 to their extended positions. The controller 177, after a predetermined time closes the valve 135 to preclude pressurized air from reaching the cylinders 32, 87. The pressurized air is exhausted through the on-off switch 46 allowing the cylinders 32, 87 to retract. The controller 177 is connected to the signal amplifier valve 175 via the conduit 179.

Figure 6:
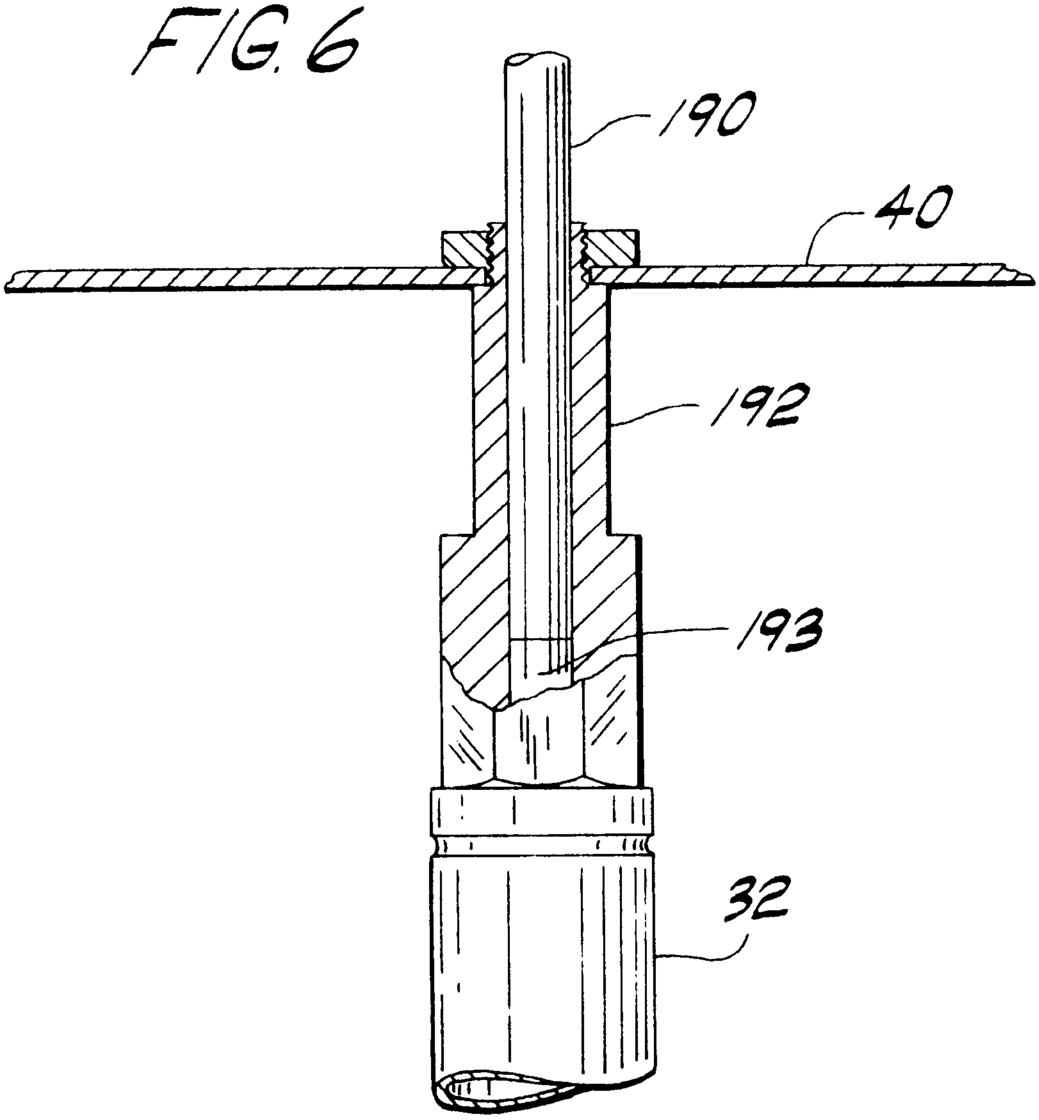
FIG. 6 is an enlarged fragmentary view of a device for agitating the inoculant.

A stand 190 is mounted on the housing 14 and is operable to support the container 30 of inoculant 29. Preferably, the container 30 is positioned at an elevated position relative to the syringe 16 for gravity flow assistance. Means can be provided for keeping the inoculant 29 mixed in the container 30 during operation of the apparatus 14. Preferably, the means is carried by the case 51 and is operable to continuously mix or agitate the inoculant 29 in the container 30. As best seen in FIG. 6, the stand 190 is mounted in a tube 192 that is secured to the lid 40. The cylinder 32 is mounted on the tube 190 and is preferably coaxial with the bore in which the stand 190 is mounted. As seen in FIG. 4, the cylinder 32 is connected in flow communication to the conduit 134 as is the syringe cylinder 87. Every time the syringe cylinder 87 is activated for extension, the cylinder 32 is also activated. The piston rod 193 of the cylinder 32 moves axially inside the tube 192 moving the stand 190 and container 30 up and down with each stroke. The movement mixes the inoculant 29 in the container 30 by shaking. The movement is about ¼". The vibration has been found adequate to keep components of the inoculant 29 from separating during operation of the apparatus 14. When the syringe cylinder 87 retracts, so does the cylinder 32. The cylinder 32 is then ready to be reactivated for mixing the inoculant 29.

In operation, an animal 12 such as a chick is placed in the cradle 25 tail or posterior 167 first. The tail portion 167 is placed in the opening 166 and under the crossbar 165. The abdomen is moved into engagement with the opening 174' and the nipple 140. The chick 12 is held firmly against the distal end of the nipple 140 and the valve seat at the opening 174' of the distal end 174 of the conduit 173 is partially or completely blocked, raising the air pressure in the conduit. The distal end 141 of the nipple 140 engages the abdomen area of the chick at the yolk sac which is just below or to the side of where the umbilical was attached. By pressing the abdomen against the nipple 140, the skin is stretched over the distal end 141 cinching the skin in place which facilitates entry and retraction of the needle 18. It also helps prevent subsequent leakage of fluid from the chick at the needle entry point. The signal amplifier 175 is activated by the increased air pressure which in turn activates the controller 177 and thus the extension of the cylinders 32 and 87. The needle 18 moves forward and penetrates the bird 12 and the inoculant 29 is injected into the bird, e.g., in the yolk sac. The needle 18 then retracts and the bird 12 is removed from the cradle 25. After a predetermined number of injections or needle movements, a quantity of disinfectant 147 is dispensed to the porous member 143 to replenish the supply of disinfectant in the porous member. The dispensing of disinfectant 147 to the porous member 143 preferably occurs when the counter 45 reaches 0 and is reset for the preset quantity. Resetting is accomplished by activating the counter reset 47. The needle cleaning occurs during operation of the apparatus 14 and the disinfectant 147 is contained during dispensing and application to the needle 18.

The operating control system is shown in FIG. 4. The system includes the source 133 of pressurized air. It is connected by a conduit 181 to the pressure regulator 137 which preferably includes an air filter device such as a Norgren model B07-101-mika. The pressure regulator 137 is adjusted with the knob 44. The gauge 43 is connected in the conduit 181 to show the operating pressure which is preferably in the range of between about 40 psi and about 60 psi. The main control on-off switch 46 is connected to the air supply conduit 181 and is preferably a three position valve such as a Wings model 508000. The three positions include off, on and manual. When off, no pressurized air is supplied beyond the valve 46 to the control system. When in manual, air is supplied to the cylinder 87 to move it, the syringe 16 and the needle 18 to their fully extended positions for position adjustment and/or verification of adjustment. When the valve 46 is in the on position, the control system is activated and ready to operate.

The flow passage 172 is at least partially blocked by an animal thereby increasing the pressure in the conduit 173. As described above, the distal end 174 of the conduit 173 forms a valve seat at the opening 174' and the chick functions as a valve seal element forming a valve on the distal end. The valve formed by the opening 174' and the animal 12 is characterized by an absence of a valve seat and valve seal element contained therein. The signal amplifier valve 175 is activated which in turn activates the controller 177 which is connected in flow communication to the signal amplifier by conduit 179. The controller 177 is connected in flow communication with the counter 45 at its count port Z and output signal port A by conduits 182, 183 respectively. The counter 45, if count down, has a preset quantity and counts one activation or shot and reduces the preset count or subsequent count by one. The controller 177, when activated by the signal amplifier valve 175 opens the valve 135 for a predetermined time to let pressurized air flow to the cylinders 32, 87. Also, an alarm device such as a whistle 184, such as Wings Model 512032 is connected in flow communication with the controller 177 and counter 45 by conduit 183. When the zero count is reached, i.e., a predetermined number of inoculations have been made, pressurized air flows to the whistle 184 producing an alarm sound letting the operator know that the inoculations for that round or group are completed. The valve 135 is also connected in flow communication with the controller 177 via conduit 178. Air from the controller 177 activates the valve 135 allowing air from the conduit 185 to flow thru the valve 85 and conduit 134 to the syringe and agitator cylinders 87, 32 forcing them to extend. As shown, the conduit 134 to the syringe is two piece allowing it to be separated at a coupling 186 mounted on the wall 38 so the two cases 34, 51 can be easily separated. After the cylinders 87, 32 have extended, the pressurized air is released via the on-off switch 46 and the cylinders can return to their normal retracted positions.

The counter 45 is connected at the air supply port P in flow communication with the valve 46 via conduit 187. The counter reset 47 is connected in flow communication with the conduit 187 and the counter 45 via conduit 188. When the counter reset 47 is activated, pressurized air is supplied to a reset port Y of the counter via conduit 188. The conduit 188 is two piece and includes a coupling 189 that is mounted in the wall 38 to facilitate separation of the cases 34, 51. When pressurized air is supplied to the counter 45 at the reset port Y, the counter 47 is returned to its preset number or quantity and is ready to begin a new countdown series. At reset activation, the pump cylinder 154 effects pumping of disinfectant 29 to the porous member 143 from the container 156 via conduits 67, 51. When the counter has reached the zero count, if a count down type, the system cannot be activated until the counter 45 is reset.

The control system also includes the flow regulator 176 connected in flow communication with the valve 46 via conduit 187 and to the signal amplifier 175 via conduit 173. The flow regulator 176 is operable to adjust the sensitivity needed to activate the signal amplifier valve 175. The more air that flows through the conduit 173, the less blockage of the opening 174' is needed to activate the syringe cylinder 87, agitator cylinder 32, controller 177 and counter 45. The signal amplifier 175 is also connected in flow communication with the valve 46 via conduit 187 connected to the input port P' to provide full pressure air to the downstream control circuit elements. Thus, the control circuit is completely pneumatically operated not requiring or using any electronic components.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for inoculating an animal, said apparatus comprising:

a hypodermic syringe;

a needle mounted on the syringe, said needle being movable on a drive path for injecting the animal;

a drive connected to the hypodermic syringe and operable to move the needle between a retracted position and an extended position;

a conduit for directing fluid to flow through said apparatus, said conduit having an opening positioned relative to said needle such that upon positioning the animal in the drive path of the needle, the animal at least partially blocks the opening of the conduit to at least partially restrict the flow of fluid through the conduit, said conduit extending in generally parallel relationship with the drive path of the needle at the opening of the conduit; and a trigger mechanism operatively connected to the drive for triggering the drive to move the needle from its retracted position to its extended position to inject the animal, the trigger mechanism being responsive to the restricted flow of fluid through the conduit to trigger the drive to move the needle to its extended position.

2. Apparatus as set forth in claim 1 wherein the restricted flow of fluid through the conduit changes the fluid pressure in the conduit, the trigger mechanism comprising a valve capable of sensing the change in fluid pressure in the conduit.

3. Apparatus as set forth in claim 2 further comprising a source of pressurized fluid in fluid communication with the drive and wherein the trigger mechanism is operable to selectively allow fluid from the source of pressurized fluid to flow to the drive to move the needle to its extended position.

4. Apparatus as set forth in claim 3 wherein the source of pressurized fluid comprises a source of pressurized air and the drive comprises a pneumatic cylinder, said source of pressurized air being in fluid communication with the conduit whereby the pressurized air flows out from the opening in said conduit.

5. Apparatus for injecting small animals with a fluid, the animals each has an abdominal area, said apparatus comprising:

a hypodermic syringe;

a needle mounted on the syringe, said needle being movable on a drive path for injection of said animal;

a cradle adjacent said needle and adapted for positioning an animal to be injected in a face up position relative to the needle so that an abdominal area of the animal is exposed for penetration by the needle, wherein the cradle has a longitudinal axis and the needle moves at an angle in the range of about −5° through about +5° relative to the longitudinal axis; and a drive connected to the hypodermic syringe and operable to selectively move the needle between an extended position and a retracted position.

6. Apparatus as set forth in claim 5 further including a guide having an elongate bore adapted to receive the needle therein upon movement of the needle between the extended and retracted positions, and a porous member mounted in the guide and surrounding the needle.

7. Apparatus as set forth in claim 6 including a source of disinfectant connected in flow communication with the porous member, said needle extending through a portion of the porous member.

8. Apparatus as set forth in claim 7 including a pump operably connected in flow communication between the source of disinfectant and the porous member and operable to sequentially pump disinfectant from the source of disinfectant to the porous member.

9. Apparatus for injecting small animals with a fluid, said apparatus comprising:

a housing;

a hypodermic syringe movably mounted on the housing;

a needle mounted on the syringe;

a drive connected to the syringe and operable to selectively move the needle between an extended position and a retracted position; and a positioning device positioned adjacent the needle and adapted for positioning an animal to be injected relative to the needle, said positioning device comprising a cradle extending from the housing and opening generally upwardly the cradle including an upwardly facing support surface with its lower most portion positioned at an angle in the range of about 20° through about 60° relative to horizontal the cradle further having a portion defining an opening for receiving a posterior portion of the animal to facilitate positioning the animal relative to the needle, the cradle further including a crossbar positioned adjacent to an end of the cradle most adjacent the housing and spaced from the support surface for receiving the posterior portion of the animal between the crossbar and the support surface.

10. Apparatus as set forth in claim 9 wherein the cradle is arcuate in transverse cross section.

11. Apparatus for injecting small animals with a fluid, said apparatus comprising:

a housing having an end wall;

a hypodermic syringe movably mounted in the housing;

a hollow needle mounted on the syringe and movable therewith, said needle being movable in a plane through a needle opening in the end wall;

a drive operably connected to the syringe to selectively effect movement of the needle between an extended position and a retracted position in the plane; and a retention platform mounted on the end wall and projecting out from the end wall, the retention platform having an upward opening cradle with a longitudinal axis defining an animal support surface spaced from the needle opening, the plane of movement of the needle being at an angle relative to the longitudinal axis of the cradle in the range of about −5° through about +5°, said support surface and needle being arranged such that an animal to be inoculated can be positioned face up on the support surface whereby the needle in its extended position penetrates an abdominal area of the animal.

12. Apparatus as set forth in claim 11 wherein the longitudinal axis of the cradle is at an angle relative to horizontal in the range of about 20° through about 60°.

13. Apparatus as set forth in claim 12 wherein the cradle has an end proximate the housing and a free end distal from the housing, the free end being higher than the end proximate the housing.

14. Apparatus for injecting small animals with a fluid, said apparatus comprising:

a housing;

a hypodermic syringe movably mounted in the housing;

a hollow needle mounted on the syringe;

- a work platform mounted on the housing and adapted for positioning an animal to be injected relative to the hollow needle;
- a drive mounted in said housing and connected to the hypodermic syringe and operable to selectively move the needle between an extended position and a retracted position;
- a guide tube mounted on the housing adjacent the needle and adapted for the needle to move through between the extended and retracted positions of the needle;
- a porous member mounted in the guide tube and surrounding a portion of the needle when the needle is in its extended position;
- a source of sterilizing fluid; and
- a conduit in flow communication with the porous member and the source of sterilizing fluid, the conduit being adapted to provide a sterilizing fluid from the source of sterilizing fluid to the porous member for application to the needle.

15. Apparatus as set forth in claim 14 including a pump connected in flow communication with the conduit between the source and the porous member and operable to pump sterilizing fluid from the source to the porous member.

16. Apparatus as set forth in claim 15 including a controller operably connected to the pump and operable to have the pump sequentially pump sterilizing fluid from the source to the porous member.

17. Apparatus as set forth in claim 16 wherein the porous member engages the needle during movement of the needle.

18. Apparatus for injecting small animals with a fluid, said apparatus comprising:

- a housing;
- a hypodermic syringe movably mounted in the housing;
- a hollow needle mounted on the syringe;
- a work platform mounted on the housing and adapted for positioning an animal to be injected relative to the hollow needle;
- a drive mounted in said housing and connected to the hypodermic syringe and operable to selectively move the needle between an extended position and a retracted position;
- a support mounted on the housing;
- a container of inoculant retained in the support; and
- agitator means carried by the housing and operably associated with the, support for periodically inducing vibration in the support, said support being operable to transmit the vibration to inoculant in the container to agitate the inoculant.

19. Apparatus as set forth in claim 18 including a source of pressurized fluid connected in flow communication with the drive and the agitator means, said agitator means including a cylinder associated with the support whereby extension of the cylinder moves the container by moving said support.

20. Apparatus as set forth in claim 19 including a controller operably connected to the cylinder and operable to effect sequential extension of the cylinder.

21. Apparatus as set forth in claim 20 wherein the controller effects extension of the cylinder when the drive moves the needle.

* * * * *